US012502304B2

(12) United States Patent
Sun

(10) Patent No.: US 12,502,304 B2

(45) Date of Patent: Dec. 23, 2025

(54) ANTI-SNORING DEVICE BASED ON EXPANSION TYPE SILENCER

(71) Applicant: Ruifeng Sun, HuaiNan (CN)

(72) Inventor: Ruifeng Sun, HuaiNan (CN)

( * ) Notice: Subject to any disclaimer, the term of this patent is extended or adjusted under 35 U.S.C. 154(b) by 285 days.

(21) Appl. No.: 18/566,905

(22) PCT Filed: Apr. 6, 2022

(86) PCT No.: PCT/CN2022/085427

§ 371 (c)(1),
(2) Date: Dec. 4, 2023

(87) PCT Pub. No.: WO2022/214007

PCT Pub. Date: Oct. 13, 2022

(65) Prior Publication Data

US 2024/0207086 A1 Jun. 27, 2024

(30) Foreign Application Priority Data

Apr. 6, 2021 (CN) ......................... 202110365907.8
Apr. 6, 2021 (CN) ......................... 202120683795.6
Feb. 10, 2022 (CN) ......................... 202220259385.3

(51) Int. Cl.
*A61F 5/56* (2006.01)
*A61M 16/06* (2006.01)
(Continued)

(52) U.S. Cl.
CPC ............... *A61F 5/56* (2013.01); *A61M 16/06* (2013.01); *G10K 11/02* (2013.01);
(Continued)

(58) Field of Classification Search
CPC ................ A61F 5/56; G10K 11/17823; G10K 11/17825; G10K 11/17881; G10K 11/02;
(Continued)

(56) References Cited

U.S. PATENT DOCUMENTS 5,444,786 A * 8/1995 Raviv .............. G10K 11/17837 381/71.14
5,522,382 A * 6/1996 Sullivan ............ A61M 16/0069 128/204.26

(Continued)

FOREIGN PATENT DOCUMENTS

CN 106375906 A * 2/2017 ............... H04R 3/02
CN 113066470 A * 7/2021 ....... G10K 11/17857
WO WO-2018215836 A1 * 11/2018 ........... G10K 11/178

*Primary Examiner* — David L Ton
(74) *Attorney, Agent, or Firm* — WPAT, PC

(57) ABSTRACT

The present invention provides an anti-snoring device based on an expansion type silencer, and proposes the technical solution from the respective of eliminating the "effect" in the causality of snoring. The anti-snoring device comprises an expansion chamber, a tube, and an active noise elimination module. The expansion chamber is connected to the active noise elimination module. The active noise elimination module further comprises a secondary sound source, a microphone, and a control module. The expansion chamber further comprises an opening for sealing and shielding the mouth and nose organ and forming an acoustic system of the expansion type silencer together with the sealed and shielded face skin. The tube is a respiratory airflow channel, and is an acoustic device having acoustic impedance different from that of the expansion chamber. In this way, the anti-snoring device provided in the utility model has the beneficial effects of being wide in applicability, large in noise elimination amount, wide in noise elimination bandwidth, small in size, light in weight, and low in electric energy consumption.

10 Claims, 7 Drawing Sheets

(51) Int. Cl.
*G10K 11/02* (2006.01)
*G10K 11/178* (2006.01)

(52) U.S. Cl.
CPC .. *G10K 11/17823* (2018.01); *G10K 11/17825* (2018.01); *G10K 11/17881* (2018.01); *A61M 2205/42* (2013.01); *G10K 2210/116* (2013.01); *G10K 2210/3011* (2013.01); *G10K 2210/3026* (2013.01); *G10K 2210/3027* (2013.01); *G10K 2210/3028* (2013.01); *G10K 2210/3044* (2013.01); *G10K 2210/3218* (2013.01)

(58) Field of Classification Search
CPC ..... G10K 2210/116; G10K 2210/3011; G10K 2210/3026; G10K 2210/3027; G10K 2210/3028; G10K 2210/3044; G10K 2210/3218; A61M 16/06; A61M 2205/42
See application file for complete search history.

(56) References Cited

U.S. PATENT DOCUMENTS

| | | | | |
|---|---|---|---|---|
| 2012/0145155 A1* | 6/2012 | Peake | A61M 16/0875 | 128/205.12 |
| 2012/0204887 A1* | 8/2012 | Connor | A61F 5/56 | 128/848 |
| 2017/0053637 A1* | 2/2017 | DeFranks | A47G 9/1045 | |
| 2019/0240435 A1* | 8/2019 | Anderson | A61M 16/0816 | |
| 2023/0337937 A1* | 10/2023 | Barlow | A61B 5/6803 | |

* cited by examiner

ANTI-SNORING DEVICE BASED ON EXPANSION TYPE SILENCER

BACKGROUND

Technical Field

The present invention relates to an anti-snoring device, and in particular to an anti-snoring device based on an expansion type silencer.

Related Art

According to informal statistics of a random population survey, more than 30% of adults in China snore. The snoring rate of males is 20-25%, the snoring rate of females is 5-15%, and the male-female ratio is 3:1. Furthermore, as the age increases, the snoring rate increases as well. The snoring rate of 40-64-year-old males reaches up to 60%, and the snoring rate of females reaches 40%.

An existing anti-snoring device adopts a technical solution of eliminating a "cause" in a causal relationship of snoring, i.e., a technical solution of eliminating a snoring sound source. For example, a snorer holds a device capable of dilating an airway in mouth, so that vibration and vortexes generated by a uvula are reduced, and thus, the snoring sound is alleviated or eliminated. For further example, after detecting the snoring sound, the anti-snoring device stimulates an acupuncture point of a human body, so that a respiratory muscle of the human body shrinks to change the acoustic characteristics such as a sectional area of a respiratory tract. For further example, the oral cavity of the snorer is closed by using a bandage. However, because the snoring physiology and mechanism are complex and diverse, existing technologies are hardly applied to all snorers, i.e., the applicability is poor.

In another aspect, the audio spectrum distribution of snoring is regular, and is substantially Gaussian distribution. Because the spectral energy of a human sound substantially concentrates on a frequency range of [200, 3500] Hz. The snore frequencies of a soft palate are often distributed in a range of 150-300 Hz, the frequencies of a sublingual part are often distributed in a range of 500-750 Hz, and the maximum value of the spectral distribution of the snoring sound is near 200 Hz and 600 Hz. The full frequency range [20, 5000] Hz of the snoring sound is classified. The frequency range [20, 1000] Hz is a low-mid frequency band, the frequency range [1000, 5000] Hz is a high-mid frequency band, and the energy of the snoring sound mainly concentrates on the low-mid frequency band [20, 1000] Hz.

Active noise reduction or active noise elimination, a noise reduction technology, is one of the existing technologies applied to the technical fields of earphones and automobiles. The technology generates a noise reduction sound wave equal to external noise in amplitude and opposite to external noise in phase by using a secondary sound source, and overlays and neutralizes the noise reduction sound wave with the noise sound wave in space (for example, in a cavity), so as to achieve a noise reduction effect. Its principle is as follows: all sounds have certain frequency spectra; if a sound with the frequency spectrum completely identical as that of noise to be eliminated, the noise can be completely cancelled as long as the phase is just opposite; in other words, the active noise reduction technology needs to satisfy phase frequency and amplitude frequency conditions at the same time.

First, in terms of satisfying the amplitude frequency condition, if active noise reduction is used in the frequency range [20-5000] Hz of the snoring sound, to satisfy an amplitude frequency characteristic, the requirement on performance index of the secondary sound source will be extremely high because the secondary sound source with a narrow frequency band hardly provides frequency response performance with enough bandwidth and gain in all frequency bands and needs a two frequency divisions (two bands) or three frequency divisions (three bands) system to satisfy the requirement, as a result, the size and weight of the whole active noise reduction system are large, with large power consumption.

In addition, in terms of satisfying the phase frequency condition, the noise reduction sound wave phase needs to match the noise phase, and the noise sound wave phase is related to the acoustic characteristic of the cavity. As shown in the solid-lined part in FIG. 8, in the range of [200, 500] Hz, the noise phase of the cavity jumps fast from −40 degrees to 100 degrees. The noise reduction system hardly follows the jumps of the noise phase fast to achieve a noise cancellation function but generates additional noise. In an actual application, for frequency domains higher than the jump site of the acoustic phase frequency of the cavity, a method of abandoning phase matching and reducing the amplitude of the noise reduction sound wave is adopted. In the field of snore stoppers involved in the present invention, due to dimensional restrictions on the noise eliminating cavity of a wearable snore stopper, an inherent acoustic phase jump frequency band of an expansion chamber overlaps with the maximum frequency band of the frequency spectrum of the snoring sound, so that for noise higher than 500 Hz, the noise reduction performance of the exiting active noise reduction technology used in the field of snore stopper is reduced severely, resulting in insufficient noise reduction capability of the active noise reduction technology at the high-mid frequency band. The active noise reduction technology is not applicable to the snore stopper device with wearability requirement. For convenient expression below, the active noise reduction technology is called active technology for short.

$$f_s = 1.22\frac{C_0}{d} \quad \text{Equation 1}$$

$$TL = 10 1g\left[1 + \frac{1}{4}\left(\frac{1}{m} - m\right)^2 \sin^2\left(\frac{2\pi L}{\lambda}\right)\right] \quad \text{Equation 2}$$

$$f_e = \frac{2n-1}{4}\frac{c_0}{L}. \quad \text{Equation 3}$$

$$f_t = \frac{n-1}{2}\frac{c_0}{L}. \quad \text{Equation 4}$$

wherein $f_s$ represents a high-frequency failure frequency;

TL represents a noise elimination amount or a transmission loss;

$f_e$ represents the maximum noise elimination frequency;

$f_t$ represents a passing frequency;

m represents an expansion ratio;

L represents a length of the expansion chamber;

λ represents a wavelength;

$c_o$ represents a sound velocity;

n=1, 2, 3, 4 . . . ; and d represents a diameter of a tube.

In the field of industrial passive silencers, as shown in FIG. 1, the expansion type silencer includes the expansion chamber 201 and the tube 202. Wherein the cross-sectional area of the expansion chamber 201 is S0, the cross-sectional area of the tube 202 is S1, and S0/S1, with the expansion ratio m=S0/S1. According to the characteristic that the acoustic impedance is discontinuous because the sectional area changes suddenly when the noise passes through the connection between the tube 202 and the expansion chamber 201, the noise in the pipeline is attenuated or reflected to the sound source. The characteristics are as follows: I, as shown in the equation 3, the maximum noise elimination frequency $f_e$ is inversely proportional to the length dimension L of the expansion chamber 201, i.e., the lower the first maximum noise elimination frequency is, the larger the length dimension L of the expansion chamber 201 is; II, as shown in the equation 2, the transmission loss TL or the noise elimination amount of the expansion type silencer is related to the expansion ratio m, i.e., it is related to the ratio of the cross section of the expansion chamber 201 to that of the tube 202. In a case where the expansion ratio m is ≥1, the greater the expansion ratio m is, the greater the transmission loss TL is. The characteristic also requires the dimension of the cross section of the expansion chamber 201 to be larger; III, a precondition that the wavelength for noise reduction is much shorter than the dimension of the expansion chamber 201 must be satisfied, with the highest failure frequency $f_s$, which results in that the dimension of the expansion chamber 201 is required to be large enough under a circumstance that the frequency spectrum of the snoring sound cannot be changed; and VI, when the wavelength for noise reduction is much larger than the dimension of the expansion chamber 201, with the lowest failure frequency $f_s$, and when the frequency is lower than $f_b$, the expansion type silencer cannot be analyzed with distributed parameters; if the equations 2-4 are not workable and centralized parameter analysis should be adopted, and at this time, the expansion type silencer is changed to a Helmholtz filtering silencer; and a connecting topological structure for the Helmholtz filtering silencer and a noise path is no longer a bypass but is serial. Therefore, the ideal working frequency range of the expansion type silencer is $[f_b, f_s]$.

According to the characteristic of the aforementioned expansion type silencer, the industrial silencer eliminates the low frequency noise, for example, noise near 100 Hz. Calculated according to the aforementioned equation 3, the length L of the silencer needs to be 85 cm, which is huge relative to the dimension of a human head which is 20 cm. Restricted by the miniaturized size and dimension due to the wearability requirement of the snore stopper, the wavelength range of the low-mid frequency band noise [20, 1000] Hz is [34, 1700] cm. According to the face dimension of the human head of an adult, the dimension of the wearable device suitable for the human head is not larger than 10 cm, and then the wavelength for noise reduction at the low frequency band is much larger than the dimension of the wearable device. Therefore, a component of the low-mid frequency band [20, 1000] Hz in the noise frequency spectrum of the snoring sound is lower than or close to the lowest failure frequency $f_b$ of the expansion type silencer, so that the noise elimination capability of the expansion type silencer is lost or the noise elimination performance is low.

In the field of an industrial active silencer, for example, the technical field of the active noise elimination of an exhaust pipe of an automobile engine, it has the following characteristics: I, the noise frequency spectrum is wide, for example, 1-10 kHz for combustion noise, 2-8 kHz for piston slap, 0.5-2 kHz for noise of a valve timing mechanism, over 2 kHz for noise of a fuel injection pump, less than 4 kHz of noise of a gear, 0.05-0.5 kHz for air inlet noise, 0.5-5 kHz for exhaust noise, 0.2-2 kHz for noise of a fan, wherein the exhaust noise is the main noise, the noise reduction working frequency band of which is much larger than that of the snore stopper; and II, the dimension of the expansion chamber 201 is large, which is much larger than that of the anti-snoring device.

As shown in FIG. 4, FIG. 5 and FIG. 6, the solid-lined part in the figures is a noise elimination characteristic curve of the active technology. The dotted line is a noise elimination characteristic curve of the expansion type silencer. To facilitate analysis, it is assumed that the noise elimination characteristics are ideal characteristics. The characteristic curve is divided into a horizontal segment and a monotonic transition segment. The key characteristic point frequencies corresponding to inflection points of the horizontal segment and the transition segment are respectively $f_0$ and $f_1$. The wearability of the snore stopper decides the dimension of the expansion chamber 201. The dimension of the expansion chamber 201 further decides the key characteristic point frequencies $f_0$ and $f_1$ of the active technology and the expansion type silencer. It is known that the larger the dimension of the expansion chamber 201 of the expansion type silencer is, the less the $f_1$ is. According to the relative relation between $f_0$ and $f_1$, the hybrid noise elimination performance of the active technology and the expanded hybrid silencer is decided. The solid line in the figures is a hybrid noise elimination characteristic curve. In the aforementioned automobile active noise elimination field, because the dimension of the expansion chamber 201 thereof is much larger than that of the expansion chamber 201 of the anti-snoring device, the hybrid noise elimination performance thereof is shown in FIG. 4, and the hybrid noise elimination performance of the anti-snoring device is shown in FIG. 5. It can be known by comparing FIG. 4 and FIG. 5 that for the silencer in the automobile field, because $f_0$ is greater than $f_1$, the noise elimination characteristic transition frequency bands of the active technology and the expansion type silencer are not overlapped, thereby not giving full play to advantages of making the best of the both worlds between the hybrid silencers, and on the contrary, the hybrid noise elimination characteristic changes suddenly at the working frequency band obviously with a narrow bandwidth.

As shown in FIG. 6, when $f_1$ is much larger than $f_0$, for example, in the application field of active noise elimination and reduction of the earphone, the dimension of the expansion chamber 201 thereof is much less than that of the expansion chamber of the snore stopper, the noise elimination characteristic transition frequency bands of the active silencer and the expansion type silencer are not overlapped or are less overlapped, thereby not giving full play to advantages of making the best of the both worlds between the hybrid silencers. On the contrary, the hybrid noise elimination characteristic changes suddenly at the working frequency band obviously with reduced noise elimination performance severely. Therefore, in the noise reduction field of the earphone, the expanded noise reduction performance of the cavity of the earphone can be ignored or is not mentioned in a literature.

The anti-snoring device provided by the present invention is restricted by the dimension of the expansion chamber required by wearability, so that $f_1$ is larger than $f_0$ but is not much larger than $f_0$, and unexpectedly, the hybrid noise elimination characteristic is like that shown in FIG. 5. The noise elimination characteristic transition frequency bands of the active silencer and the expansion type silencer are overlapped, so that the hybrid noise elimination characteristic is balanced at the working frequency band with a large bandwidth. Thus, the technical solution of the active and expanded hybrid silencers obtains an unexpected technical effect in the application field of the anti-snoring device.

In conclusion, the special frequency spectral distribution of the snoring sound and the dimensional restriction on wearability form a reciprocal contradiction for a design of an acoustic system of the anti-snoring device, which decides that the difficulty of the technical solution of the anti-snoring device for a wearable scenario provided by the present invention is miniaturization. Due to the wearability requirement on miniaturization, the expansion type silencer fails to eliminate noise or eliminates noise badly with the low-mid frequency component [20, 1000] Hz of the noise of the snoring sound. On the other hand, because it is hard to match the phase of the active silencer at the high frequency band, the noise reduction performance of the active silencer at the high-mid frequency band [1000, 5000] Hz is reduced. Therefore, it is necessary to provide a technical solution of a novel anti-snoring device in combination with advantages of the active and expansion type silencers in the technical field of anti-snoring device from the perspective of eliminating the "effect" of the causal relationship of snoring. That is, at the low-mid frequency band [20, 1000] Hz of the snoring sound, the active and expanded noise elimination modes, i.e., the hybrid noise elimination, are used at the same time. A noise elimination mode that the expanded noise elimination mode is primarily used at the high-mid frequency band [1000, 5000] Hz, and the active noise elimination mode is accessory is used. In the application field of the anti-snoring device, because of the matching ability between the dimension of the expansion chamber and the frequency band of the noise of the snoring sound, as shown in FIG. 5, the unexpected technical effect is obtained, i.e., the noise elimination and noise-reducing frequency band is wide and flat. The present invention provides a anti-snoring device based on an expansion type silencer.

It can be appreciated that the demarcation point 1000 Hz of the high-mid frequency band is a parameter controlled by the length dimension L of the expansion chamber. The larger the length L of the expansion chamber is, the more deviation of the demarcation point of the high-mid frequency band toward a high frequency end. The equivalent value of the length dimension of the expansion chamber corresponding to the demarcation point 1000 Hz is 5 cm. To facilitate expression, 1000 Hz is used below as the demarcation point between the low-mid frequency and the high-mid frequency.

SUMMARY

However, the vocabulary expression of the present invention is only used to describe some embodiments (whether or not already in the claims) disclosed in this specification, rather than a complete description of all possible embodiments.

In order to achieve the above purposes, the present invention is to provide a anti-snoring device based on an expansion type silencer. To overcome the deficiencies of poor adaptability, low noise elimination performance, large size, heavy weight, high energy consumption, and the like in the prior art, a technical solution is proposed from the perspective of an "effect" in a causal relationship. One side of an expansion chamber is opened for hermetically shielding oronasal organs and forming an acoustic system of the expansion type silencer with hermetically shielded facial skin. In the technical field of anti-snoring device, a technical solution of a novel anti-snoring device in combination with advantages of the active and expansion type silencers is provided. In the low-mid frequency band of the snoring sound, the active and expanded noise elimination modes are used at the same time, i.e., hybrid noise elimination. A noise elimination mode that the expanded noise elimination mode is primarily used at the high-mid frequency band, and the active noise elimination mode is accessory is used to achieve the anti-snoring device based on the expansion type silencer.

The present invention is achieved as follows: a anti-snoring device based on an expansion type silencer includes an expansion chamber, a tube and an active noise elimination module, wherein the expansion chamber is connected to the active noise elimination module; the active noise elimination module further includes a secondary sound source, a microphone and a control module; the tube is an airflow passage for breathing, which is an acoustic device with acoustic impedance different from that of the expansion chamber; the anti-snoring device further includes an opening for hermetically shielding oronasal organs and forming an acoustic system of the expansion type silencer with hermetically shielded facial skin, and a division board which divides the anti-snoring device into the front expansion chamber and a rear isolation chamber connected on an airway.

Preferably, the active noise elimination module and the expansion chamber are detachably connected.

Preferably, noise of a snoring sound is first subjected to the isolation chamber to remove high-mid frequency components, and is then subjected to the expansion chamber to remove low-mid frequency components.

Preferably, the control module further includes an audio bypass module. Audio input by the bypass module generates a sound wave in the expansion chamber through the secondary sound source, noise of the sound wave is not actively eliminated, the sound wave enters a nasal cavity, and is then propagated to the inner side of an eardrum through an auditory tube and a middle ear cavity to cause vibration of the eardrum, so that a human has an auditory sense.

Preferably, the anti-snoring device further includes a Bluetooth module respectively connected to the audio bypass module and external wireless equipment. The Bluetooth module inputs an audio signal from the external wireless equipment and then outputs the audio signal to the audio bypass module. The external wireless equipment includes a mobile phone, a computer and a tablet personal computer.

Preferably, the anti-snoring device further includes a voice pickup microphone connected to the Bluetooth module to pick up a human sound audio signal, and then the Bluetooth module outputs the human sound audio signal to the external wireless equipment.

Preferably, the active noise elimination module can close noise elimination of the high-frequency components of the noise of the snoring sound.

Preferably, topological structures of the microphone and the control module include feedforward, feedback and hybrid structures.

Preferably, the microphone is connected to one of or a combination of the front expansion chamber, the rear isolation chamber and the tube.

The present invention has the following beneficial effects:

The present invention provides a anti-snoring device based on an expansion type silencer. First, the technical solution is proposed from the perspective of eliminating the "effect" in the causal relationship of snoring. In the technical field of expansion type silencer, by adopting the noise elimination mode of expanded and active silencers, the technical deficiency that the noise elimination performance of the active silencer at the high-mid frequency band is reduced, the noise elimination performance of the expansion type silencer at the low-mid frequency band is reduced, and the bandwidth is insufficient is overcome, so that the anti-snoring device provided by the present invention gains beneficial effects of wide applicability, large noise elimination amount, wide noise elimination bandwidth, small size, light weight, and low electric energy consumption. Then, the active noise elimination module is detachably connected to the expansion chamber, which solves the problem of a peculiar smell caused by breathing when the expansion chamber is cleaned; further, the control module further includes the audio bypass module which propagates the sound wave converted by the audio to the inner side of the eardrum through the nasal cavity, the auditory tube and the middle ear cavity to cause vibration of the eardrum, so that the human has the auditory sense, which solves the problem that the earphone is easy to fall off when the human sleeps at a prone position. Finally, a serial dual-cavity acoustic construction is formed by additionally arranging the isolation chamber, which solves the problem of stability of noise elimination performance caused by mouth opening and closing behaviors and air leakage.

BRIEF DESCRIPTION OF THE DRAWINGS

In order to more clearly explain the embodiment of the present disclosure or the technical scheme in the prior art, the following will briefly introduce the attached drawings that need to be used in the embodiment. It is obvious that the attached drawings in the following description are only some embodiments of the present disclosure. For ordinary technicians in the art, without paying creative labor, other drawings can also be obtained from these drawings.

DETAILED DESCRIPTION

In order to more clearly explain the embodiment of the present disclosure or the technical scheme in the prior art, the following will briefly introduce the attached drawings that need to be used in the embodiment. It is obvious that the attached drawings in the following description are only some embodiments of the present disclosure. For ordinary technicians in the art, without paying creative labor, other drawings can also be obtained from these drawings.

Figure 1:
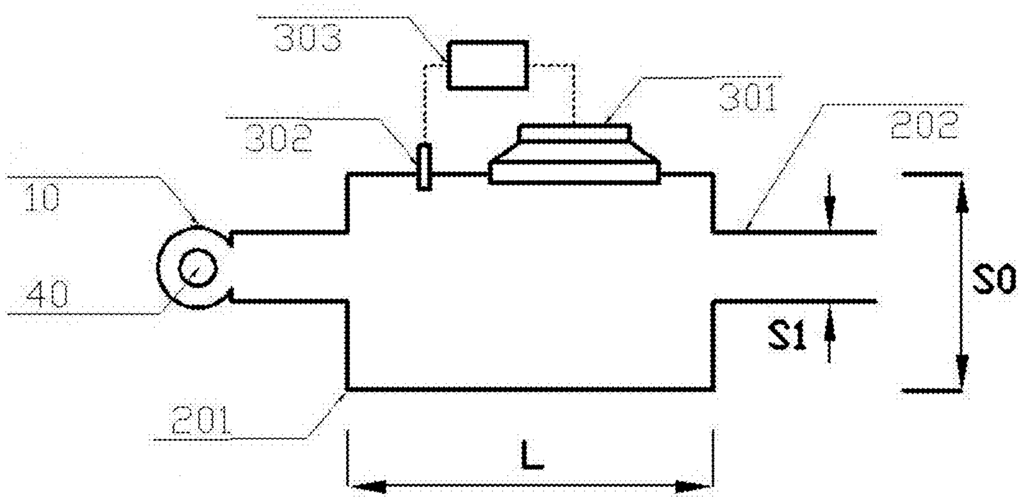
FIG. 1 is a schematic diagram.
Figure 7:
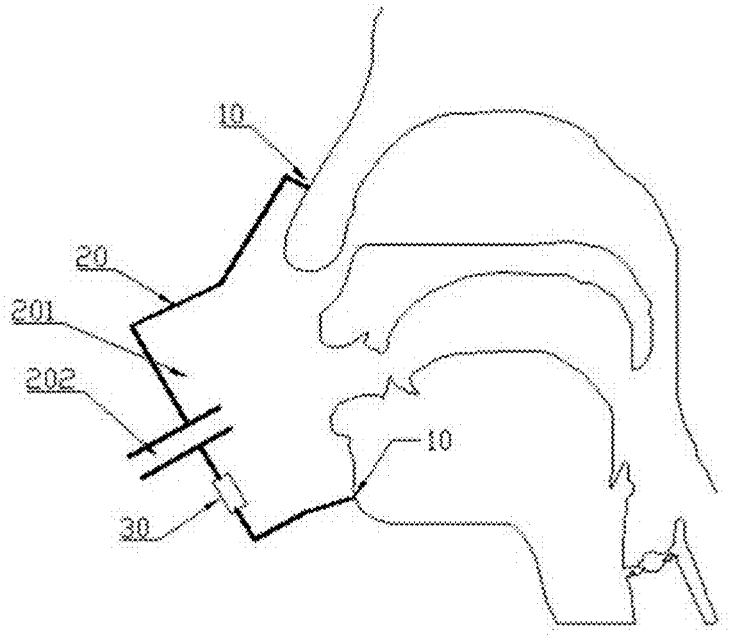
FIG. 7 is a schematic diagram of a first embodiment worn.
Figure 8:
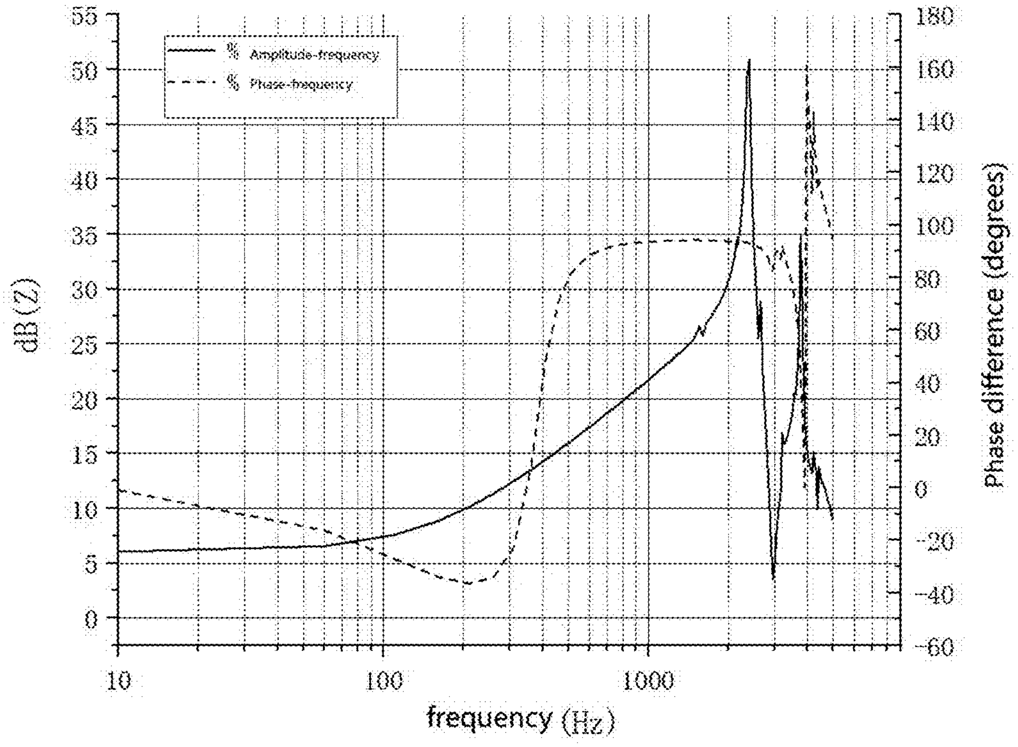
FIG. 8 is an acoustic phase frequency characteristic diagram of an expansion type silencer.

A configuration of a wearable anti-snoring device provided by the present invention is shown in FIG. 7. An expansion chamber 201 is a semi-closed cavity opened at one side and jointly forms a closed expanded acoustic noise elimination cavity with hermetically shielded facial skin tissues. Due to mechanical elasticity and tissue friction force of skin, the acoustic capacitance of the expansion chamber 201 and the acoustic resistance of passively absorbed noise are equivalently increased, which equivalently increases the size and sound absorption material of the expansion chamber 201, and the acoustic system is shown in FIG. 1 and FIG. 7. Geometric structural parameters shown in FIG. 7 are assumed to analyze and elaborate the implementation principle of the present invention. The inner cavity volume of the expansion chamber 201 is 125 $cm^3$, the tube 202 is an air outlet pipe with the inner diameter of 10 mm, and three transmission loss curves are calculated by simulating the expanded, active and hybrid silencers through the finite element. The expanded technology refers to a condition of using the expansion type silencer only to eliminate noise without using the active noise elimination module 30 at the same time. The transmission loss TL (the noise elimination amount) is shown in the solid line in FIG. 2. The transmission loss of the noise of the snoring sound is narrow in bandwidth, for example, the transmission loss at the low-mid frequency [20-500] Hz is € [5-16] dB, and the noise elimination amount at the first maximum noise elimination point 2410 Hz is 50 dB, which indicates that under the condition that the wearable dimension is restricted, unlike silencers in other technical fields, the frequency of the first noise elimination point cannot be reduced and the transmission loss bandwidth and the noise elimination amount less than those at the frequency and of the noise elimination point cannot be improved by increasing the size dimension of the expansion chamber 201.

Therefore, at the low-mid frequency band with the failed or bad expansion type silencer, the expander silencer and the active noise elimination module work at the same time. For example, the microphone and the control module use the feedforward topological structures. The microphone 302 collects a noise signal of the snoring sound, and after the signal is processed by the control module, the secondary sound source is then driven to send out an inverted sound wave which counteracts with the noise signal of the snoring sound within the cavity of the expansion chamber 201 to achieve the purpose of stopping snoring and eliminating the noise. The transmission loss calculated by simulation is shown in the dotted line in FIG. 2. In the range of [100 Hz, 1460] Hz, the acoustic effects of the active noise elimination module and the expansion type silencer are overlapped, and the transmission loss, i.e., the noise elimination amount, is reduced monotonically in performance. The transmission loss of the monotonic active noise elimination module is shown in the dot dash line in FIG. 2, and the transmission loss (the noise elimination amount) at the frequency band larger than 500 Hz is reduced obviously. The loss curve of the monotonic expanded noise elimination is shown in the solid line in FIG. 2, and the transmission loss is low at the low-mid frequency band. Particularly in the range of [20, 100] Hz, the transmission loss is close to or lower than the minimum discernible hearing of the human, i.e., a difference of 3 dB.

Figure 2:
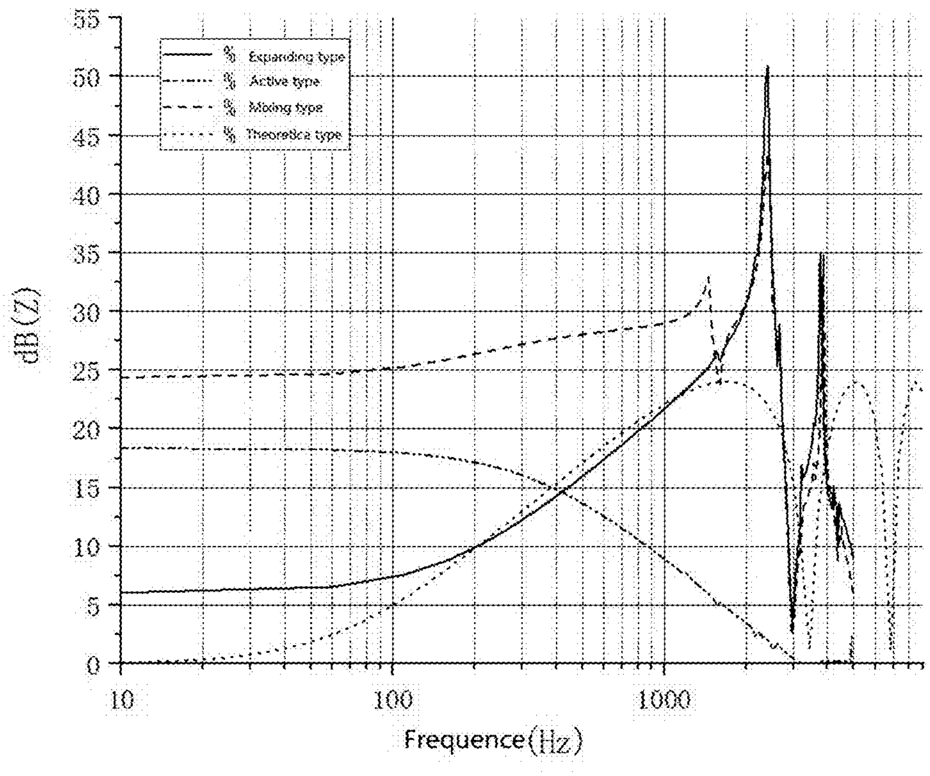
FIG. 2 is a comparison diagram of a transmission loss.

As shown in the dotted line in FIG. 2, it shows a theoretical value of the noise elimination amount of the expansion type silencer calculated according to the aforementioned equation 2. Compared with a finite element simulation value of the expansion type silencer shown in the solid line in FIG. 2, at the low frequency band ≤200 Hz, the theoretical value is lower than the simulation value, indicating that the expansion type silencer starts to be gradually transformed into the Helmholtz filtering silencer. Therefore, all frequency bands of the snoring sound [20, 5000] Hz can be divided into a Helmholtz filter stage of [20, 200] Hz, an expansion type silencer preceding stage of [200, 1460] Hz and an expansion type silencer post stage of [1460, 5000] Hz according to the configuration of the resistance silencer. 1460 Hz here is the demarcation point between the low-mid frequency band and the high-mid frequency band related to the length L parameter of the expansion type silencer in a specific application. To facilitate expression, because the frequency spectral energy of 80% of snoring sounds concentrates on [20, 1000] Hz, 1000 Hz is still taken as the demarcation point for the high-mid frequency band.

At the high-mid frequency band of [500, 5000] Hz, the transmission loss or noise elimination amount is most contributed by the expansion type silencer. As shown in FIG. 2, when the frequency of the noise is larger than 1610 Hz, the active noise elimination module less affects the transmission loss curve at the high-mid frequency band. Therefore, for the component with the noise of the snoring sound larger than 1610 Hz, the active noise elimination module of the anti-snoring device provided by the present invention can stop noise elimination, so that 20% of power consumption can be saved. Compared with the single active silencer, the anti-snoring device provided by the present invention has the advantages of low power consumption, low requirement on electroacoustic performance parameter of the secondary sound source and light structural weight. It is to be specially announced that at the high-mid frequency band, closing of the active noise elimination module is the optimal energy-saving solution which is not equivalent to closing of the active noise elimination module as necessity. Therefore, at the high-mid frequency band, still use of the active noise elimination module is also regarded as modifications, equivalent substitutions, improvements, and the like made within the spirit and principle of the present invention, which should all fall into the protection scope of the present invention.

Figure 3:
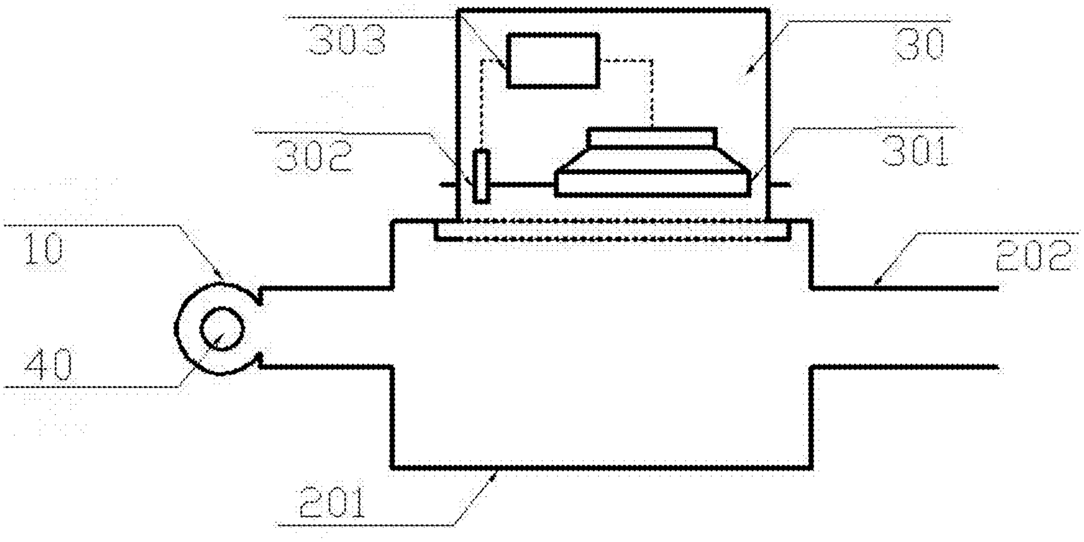
FIG. 3 is a schematic diagram of a detachable active noise elimination module.

It is to be understood that the dimension of the expansion chamber is $125^{1/3}$=5 cm which is much less than the noise wavelength (34-1700 cm) at the low-mid frequency band [20, 1000] Hz. The noise elimination amount and the bandwidth performance of the expansion type silencer at the low-mid frequency band [20, 1000] Hz are reduced. With decrease of the frequency, it is gradually transformed into a Helmholtz acoustic filter. At the low-mid frequency band, analysis of the sound field in the expansion chamber does not accord with the condition of distribution parameters, so that concentrated parameter analysis should be adopted. In the concentrated parameters, a wave equation in the sound field can be considered a one-variable function of time and is irrelevant to the spatial space. Therefore, the secondary sound source is irrelevant to the mounting position and the active noise reduction performance of the microphone. Then, the microphone and the secondary sound source which can be mounted in close positions can be designed as a module, which provides probability for detachability requirements of the active noise elimination module. As a silencer for human breathing, under a circumstance of multiple times of use, a peculiar smell will be generated due to breathing in the expansion chamber. The active noise elimination module is an electronic device which has to avoid inundation. As shown in FIG. 3, after the active noise elimination module 30 and the expansion chamber 201 are detached and separated, the expansion chamber 201 can be cleaned with water.

It is to be understood that the size dimension of the expansion chamber 201 is crucial to performance of the anti-snoring device. If the expansion chamber 201 is large in size dimension, although better noise elimination amount and bandwidth performance can be obtained, the wearability will be reduced. The expansion chamber 201 is small in size dimension. Although the wearability is improved, the noise elimination amount and the bandwidth of the anti-snoring device will be reduced. The size of the expansion chamber is reduced in a limiting case because the diameter of the pipe is restricted by the dimension of the nostrils or face [2] and cannot change greatly. Finally, the size of the expansion chamber 201 is reduced to show the expansion ratio of the expansion type silencer $m \leq 1$, which is also regarded as modifications, equivalent substitutions, improvements, and the like made within the spirit and principle of the present invention, all of which should fall into the protection scope of the present invention.

It is to be understood that in a case that $m>1$, to improve the wearability, the size of the expansion chamber is further reduced. The expansion ratio is reduced continuously. Compared with the active noise elimination amount, the expanded noise elimination amount contributes less to the snore stopper and the snore stopper is approximately regarded as the active silencer, which is regarded as modifications, equivalent substitutions, improvements, and the like made within the spirit and principle of the present invention, all of which should fall into the protection scope of the present invention.

Figure 4:
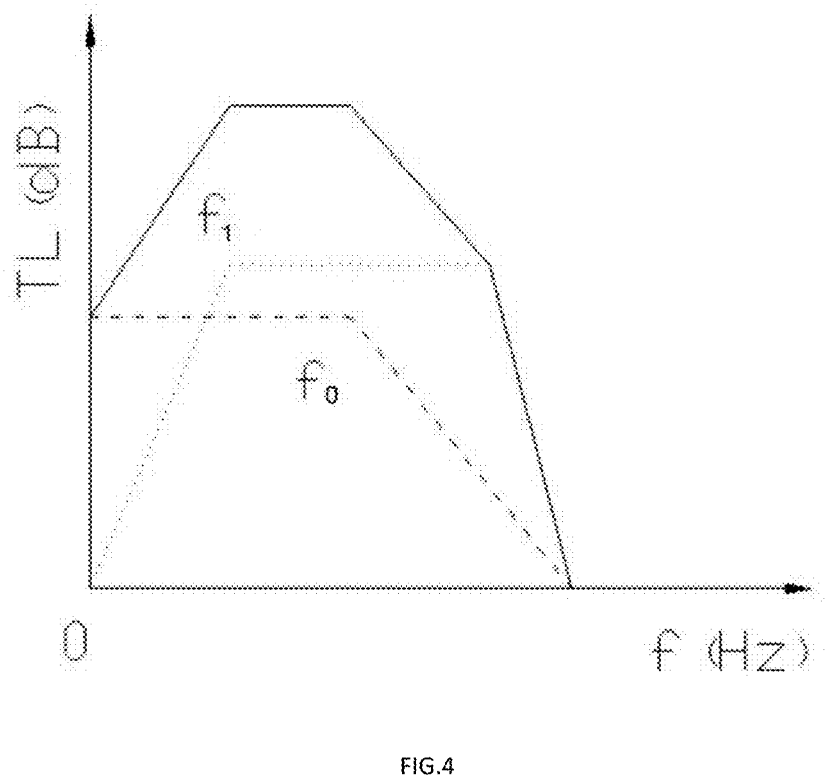
FIG. 4 is a hybrid noise elimination characteristic diagram with $f_1$ less than $f_0$.
Figure 5:
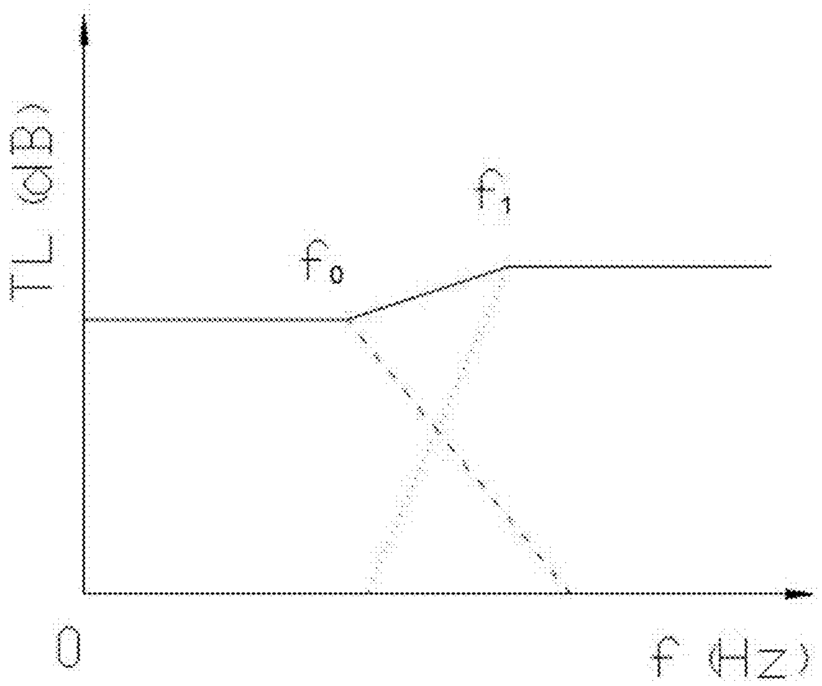
FIG. 5 is a hybrid noise elimination characteristic diagram with $f_1$ larger than $f_0$ but not much larger than $f_0$.
Figure 6:
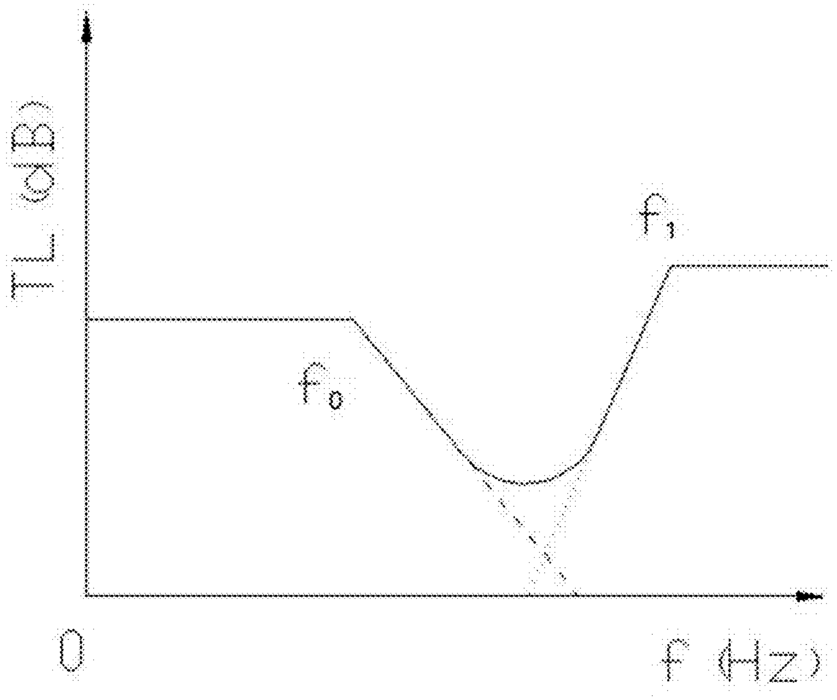
FIG. 6 is a hybrid noise elimination characteristic diagram with $f_1$ much larger than $f_0$.

As shown in FIG. 4, FIG. 5 and FIG. 6, the solid-lined part in the figures is a noise elimination characteristic curve of the active technology. The dotted line is a noise elimination characteristic curve of the expansion type silencer. To facilitate analysis, it is assumed that the noise elimination characteristics are ideal characteristics. The characteristic curve is divided into a horizontal segment and a monotonic transition segment. The key characteristic point frequencies corresponding to inflection points of the horizontal segment and the transition segment are respectively $f_0$ and $f_1$. The wearability of the anti-snoring device decides the dimension of the expansion chamber 201. The dimension of the expansion chamber 201 further decides the key characteristic point frequencies $f_0$ and $f_1$ of the active technology and the expansion type silencer. It is known that the larger the dimension of the expansion chamber of the expansion type silencer is, the less the $f_1$ is. According to the relative relation between $f_0$ and $f_1$, the hybrid noise elimination performance of the active technology and the expanded hybrid silencer is decided. The solid line in the figures is a hybrid noise elimination characteristic curve. In the aforementioned automobile active noise elimination field, because the dimension of the expansion chamber 201 thereof is much larger than that of the expansion chamber 201 of the anti-snoring device, the hybrid noise elimination performance thereof is shown in FIG. 4, and the hybrid noise elimination performance of the anti-snoring device is shown in FIG. 5. It can be known by comparing FIG. 4 and FIG. 5 that for the silencer in the automobile field, because $f_0$ is greater than $f_1$, the noise elimination characteristic transition frequency bands of the active technology and the expansion type silencer are not overlapped, thereby not giving full play to advantages of making the best of the both worlds between the hybrid silencers, and on the contrary, the hybrid noise elimination characteristic changes suddenly at the working frequency band obviously with a narrow bandwidth.

As shown in FIG. 6, when $f_1$ is much larger than $f_0$, for example, in the application field of active noise elimination and reduction of the earphone, the noise elimination characteristic transition frequency bands of the active silencer and the expansion type silencer are not overlapped or are less overlapped, thereby not giving full play to advantages of making the best of the both devices between the hybrid silencers. On the contrary, the hybrid noise elimination characteristic changes suddenly at the working frequency band obviously with reduced noise elimination performance severely. Therefore, in the noise reduction field of the earphone, the expanded noise reduction performance of the cavity of the earphone can be ignored or is not mentioned in a literature.

The anti-snoring device provided by the present invention is restricted by the dimension of the expansion chamber 201 required by wearability, so that $f_1$ is larger than $f_0$ but is not much larger than $f_0$, and unexpectedly, the hybrid noise elimination characteristic is like that shown in FIG. 5. The noise elimination characteristic transition frequency bands of the active technology and the expansion type silencer area overlapped, so that the hybrid noise elimination characteristic is balanced at the working frequency band with a large bandwidth. Thus, the technical solution of the active and expanded hybrid silencers obtains an unexpected technical effect in the application field of the anti-snoring device.

It is to be understood that topological structures of the microphone 302 and the control module 303 include feedforward and feedback structures, and a hybrid structure of the feedforward and feedback structures.

It is to be understood that the tube 202 is the acoustic device with the acoustic impedance different from that of the expansion chamber 201; the impedance generated at the connection between the tube 202 and the expansion chamber 201 are discontinuous. Therefore, the shape of the tube 202 is not limited to the shape concept of the geometric structure. In other words, the tube 202 can be any acoustic device, the acoustic impedance of which is discontinuous with that of the expansion chamber 201, including a porous structural device. For example, as shown in FIG. 7, the opening 10 of the expansion chamber 201 is sealed and shields the oronasal organs. The opening 10 and the facial skin shielded thereby jointly form the expansion chamber 201. The section thereof with an interface of the nostril changes suddenly, and the acoustic impedance is discontinuous, and at the time, the structure of the nostril is the tube 202.

In conclusion, the anti-snoring device provided by the present invention integrates advantages of the expansion type silencer and the active silencer and avoids deficiencies of the two. Moreover, restricted by the dimension of the expansion chamber 201 required by wearability, the hybrid noise elimination characteristic is unexpectedly like that shown in FIG. 5. The noise elimination characteristic transition frequency bands of the active silencer and the expansion type silencer are overlapped, so that the hybrid noise elimination characteristic is balanced at the working frequency band with a large bandwidth. Thus, the technical solution of the active and expanded hybrid silencers obtains an unexpected technical effect in the application field of the anti-snoring device. The performance of large noise elimination amount, high bandwidth, small size, light weight and low electric energy consumption is improved. In addition, the active noise elimination module and the expansion chamber 201 of the anti-snoring device provided by the present invention are detachably connected, which solves the problem that the breathing peculiar smell when the expansion chamber 201 is cleaned is solved.

Figure 10:
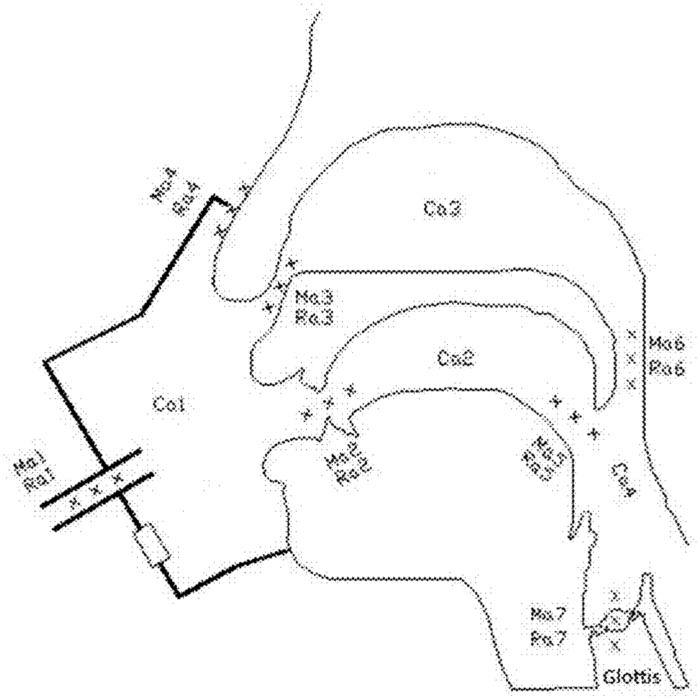
FIG. 10 is a pattern diagram of an acoustic system without an isolation chamber.
Figure 11:
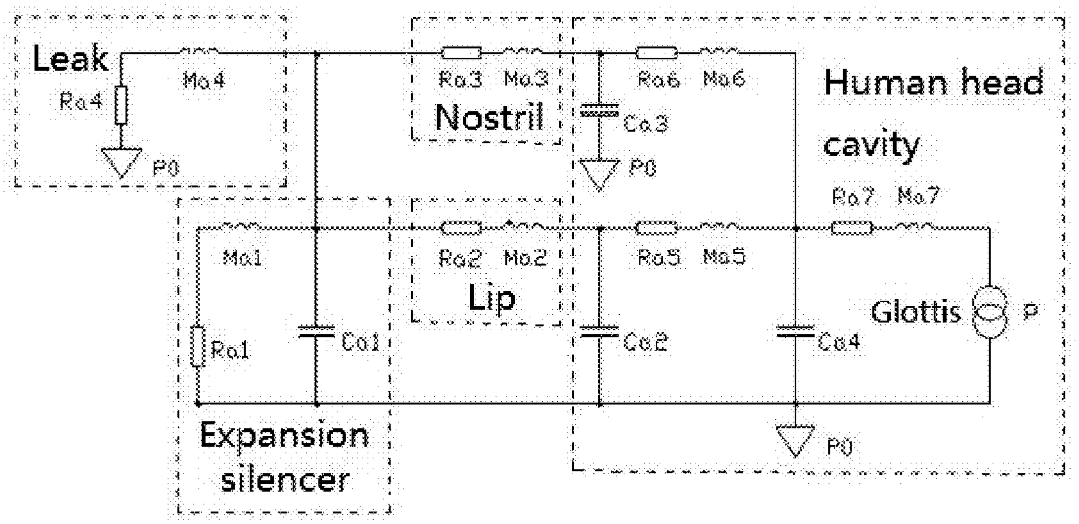
FIG. 11 is a mouth opening acoustoelectric analog circuit diagram without the isolation chamber.
Figure 12:
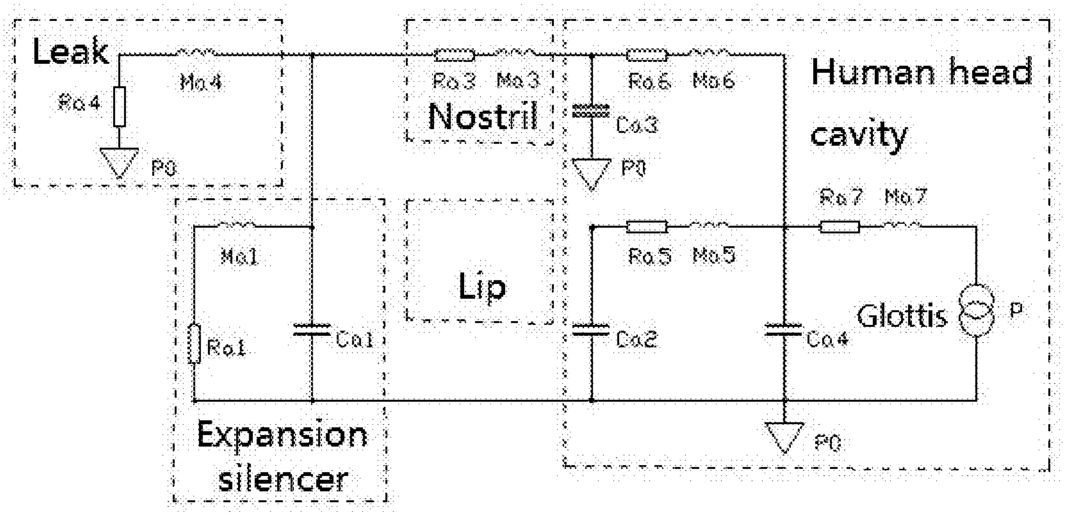
FIG. 12 is a mouth closing acoustoelectric analog circuit diagram without the isolation chamber.

On the other hand, the snoring organs 40 include the nose and the mouth. When the mouth opens and closes periodically during snoring, its acoustic system of the mouth is shown in FIG. 10. When the mouth closes, in a working environment of the active noise elimination module 30, an acoustic capacitance Ca1 of the expansion chamber 201, and an acoustical mass Ma1 and acoustic resistance Ra1 of the pipe 202, mainly form an acoustic impedance network, an electroacoustic analog diagram of which is shown in FIG. 12; when the mouth opens, an acoustic capacitance Ca2 of the oral cavity, an acoustic mass Ma2 and acoustic resistance Ra2 of a lip, an acoustic capacitance Ca1 of the expansion chamber, and the acoustical mass Ma1 and the acoustic resistance Ra1 of the tube 202 form an acoustic impedance network, an electroacoustic analog diagram of which is shown in FIG. 11. It can be known by comparing FIG. 11 and FIG. 12 that when the mouth opens or closes, the acoustic capacitance Ca2 acoustically corresponding to the oral cavity is connected parallel to or disconnected to the acoustic capacitance Ca1 of the expansion type silencer, and meanwhile, the acoustic mass Ma2 corresponding to the lip is serially connected to or disconnected to the acoustic mass Ma1 of the expansion type silencer, which results in that the opening or closing state of the mouth has a huge influence on the working environment of the active noise elimination module 30, so that the stable noise reduction performance is hardly kept. In the application fields such as an industrial silencer, automobile active noise elimination and earphone noise reduction, the acoustic parameters of the expansion chamber 201 will not be changed due to human behaviors, so that the parameters are constant.

Meanwhile, as shown in FIG. 10, because there is air leakage between the opening 10 of the expansion chamber and the skin hermetically contact with the opening, the acoustic characteristic of the expansion chamber 201 can be equivalent with the acoustic mass Ma4 and the acoustic impedance Ra4, the electroacoustic analog of which is shown in FIG. 11. After the acoustic mass Ma4 and the acoustic impedance Ra4 are connected in series, they are then connected in parallel to the acoustic capacity Ca1 of the expansion chamber 201, which directly affects the working environment of the active noise reduction module 30.

Figure 9:
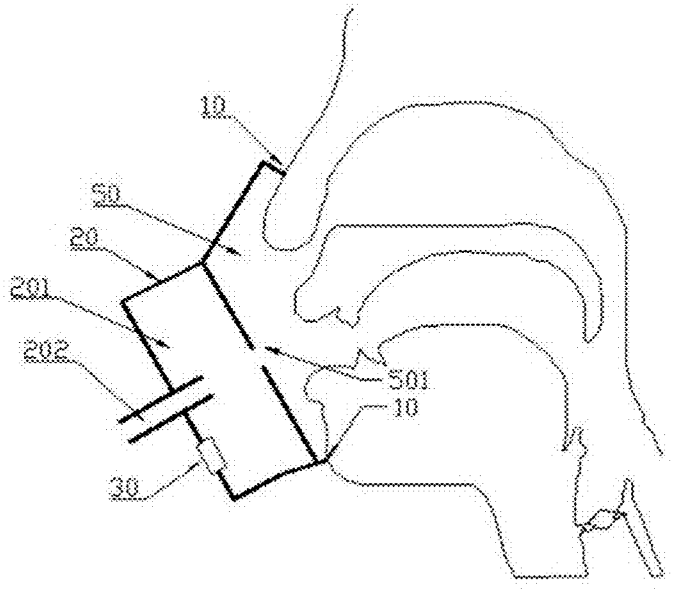
FIG. 9 is a schematic diagram of a second embodiment.
Figure 13:
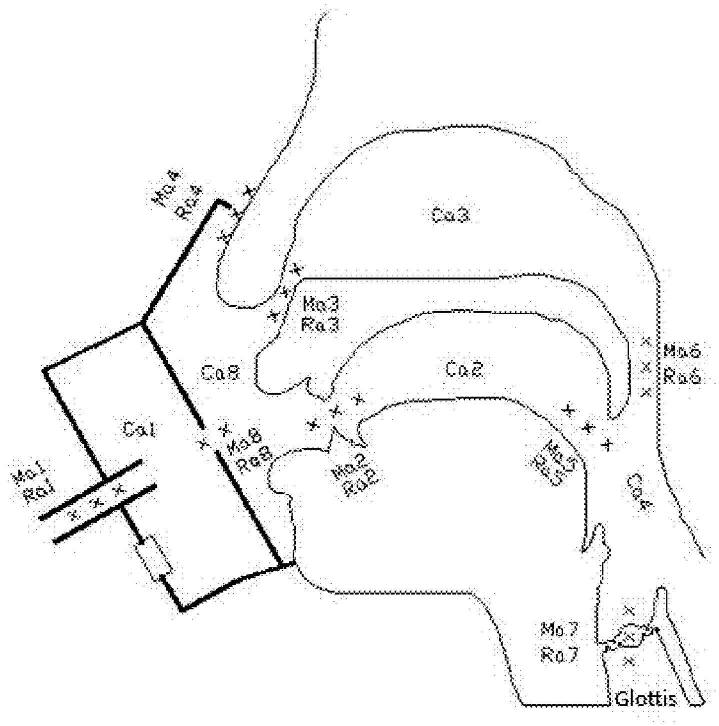
FIG. 13 is a pattern diagram of an acoustic system with the isolation chamber.
Figure 14:
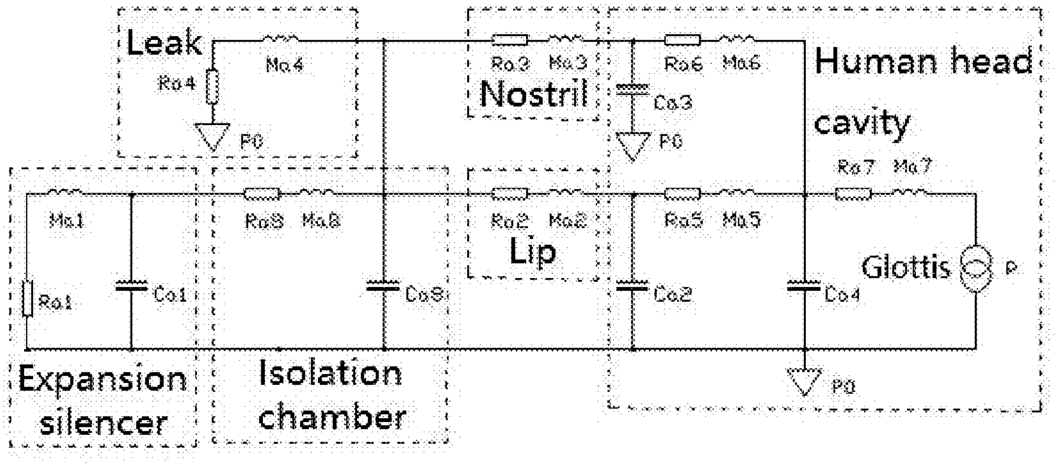
FIG. 14 is a mouth opening acoustoelectric analog circuit diagram with the isolation chamber.

To solve the problem caused by the mouth opening and closing behaviors and the air leakage, the dual-cavity acoustic structure is adopted, i.e., the isolation chamber 50 is additionally arranged and is connected serially with the expansion chamber 201, with vent holes or vent pipes connected in the airway between the isolation chamber 50 and the expansion chamber 201. The acoustic system of which is shown in FIGS. 9 and 13, and an electroacoustic analog line of which is shown in FIG. 14. It can be known from FIG. 14 that by adjusting parameters of an acoustic mass Ma8 of the vent holes or vent pipes and an acoustic capacitance Ca8 of the isolation chamber 50, within a set noise reduction working frequency band, the huge influence of the month opening or closing state and the air leakage on the working environment of the active noise elimination module 30 can be reduced to keep the stable noise reduction performance, for example, by adjusting the acoustic mass Ma8 of the isolation chamber 50, the influence of parameter change of the acoustic mass Ma2 of the lip on the acoustic characteristic of the expansion chamber 201 can be weakened. Because the acoustic mass Ma8 of the isolation chamber 50 is inversely proportional to the pore diameter of the vent hole or the pipe diameter of the vent pipe on the division board 501 and is directly proportional to the thickness of the vent hole or the pipe length of the vent pipe, Ma8 can be increased, so that the Ma8 is relatively much larger than an equivalent acoustic mass obtained by overlapping Ma2 and Ma4, and therefore, the influence of the change of the equivalent acoustic mass caused by the mouth opening and closing behaviors and the air leakage on the acoustic characteristic parameters of the expansion chamber is weakened or can be ignored. Meanwhile, the acoustic mass Ma8 of the isolation chamber 50 as an inductive element counteracts the acoustic capacitance Ca2 of the oral cavity as a capacitive element, so that the influence of the change of the equivalent acoustic mass caused by the mouth opening and closing behaviors and the air leakage on the acoustic characteristic parameters of the expansion chamber is weakened or can be ignored. As shown in FIGS. 13 and 14, Ma1 and Ra1 respectively represent the acoustic mass and the acoustic impedance of tube 202, Ma3 and Ra3 respectively represent the acoustic mass and the acoustic impedance of the nostril, Ca3 represents the acoustic capacitance of the nasal cavity, Ca4 represents the acoustic capacitance of the trachea, Ma5 and Ra5 respectively represent the acoustic mass and the acoustic impedance of the junction between the oral cavity and the trachea, Ma6 and Ra6 respectively represent the acoustic mass and acoustic impedance of the junction between the oral cavity and the trachea, Ma7 and Ra7 respectively represent the acoustic mass and acoustic impedance of the trachea, and Ma8 and Ra8 respectively represent the acoustic mass and acoustic impedance of the vent holes or vent pipes.

From discussion of the dual-cavity acoustic structure, a further improved solution is the dual-cavity acoustic structure. According to the characteristics of the frequency spectra of noise of different snoring sounds and their noise elimination principles, noise is reduced at different frequency bands. The noise of the snoring sound is first subjected to the isolation chamber 50 to eliminate the high-mid frequency noise and then subjected to the expansion chamber 201 and the active silencer to eliminate the low-mid frequency noise. Therefore, the size dimension of the expansion chamber 201 can be made relatively small, and the size dimension of the isolation chamber can be made relatively large.

In conclusion, according to the anti-snoring device provided by the present invention, the periodical behaviors of the mouth and the air leakage are another difficulty to design the snore stopper. By adopting the technical solution with the isolation chamber forming the dual-cavity acoustic structure, by adjusting the parameters such as the acoustic mass of the vent holes or vent pipes and the acoustic capacitance of the isolation chamber 50, within the set noise reduction working frequency band, the huge influence of the month opening or closing state and the air leakage on the working environment of the active noise elimination module 30 can be reduced to keep the stable noise reduction performance and improve the adaptability of individual difference of a user group. A further improved solution is division of labor cooperation for the working frequency band, noise elimination acoustic and electronic functional modules of the dual cavities to improve the noise reduction and adaptability of the snore stopper according to the characteristics of the frequency spectra of different snoring noise and their noise elimination principles.

In addition, when the sleeping posture is the prone position, if a user needs to listen to music or answer calls, a conventional mode is to use an earphone which is easy to fall off at the prone position. When the anti-snoring device provided by the present invention is used, the control module 303 further includes an audio bypass module (not shown in the figures). Audio input by the bypass module or answer calls, a conventional mode is to use the earphone which is easy to fall off at the prone position. When the anti-snoring device provided by the present invention is used, the control module further includes the audio bypass module. The audio inputted by the audio bypass module generates a sound wave in the expansion chamber through the secondary sound source, noise of the sound wave is not actively eliminated, the sound wave enters a nasal cavity, and is then propagated to the inner side of an eardrum through an auditory tube and a middle ear cavity to cause vibration of the eardrum, so that a human has an auditory sense. In other words, the anti-snoring device provided by the present invention has the function of replacing the earphone at the prone position.

Specifically, as shown in FIG. 7, the present invention provides a first embodiment of a anti-snoring device based on an expansion type silencer, including an expansion type silencer 20 and an active noise elimination module 30, wherein the expansion chamber 201 has an edge of an opening 10 of the expansion chamber. The edge is made of a medical grade soft silica gel material, so that it keeps a good sealing property with facial skin. The tube 202 is taken as an air inlet/outlet pipe for breathing, wherein the inner diameter is 10 mm. the volume of the expansion chamber 201 is 125 $cm^3$, the length of the expansion chamber 201 is ≈5 cm, and the expansion ratio is m≈32.

The expansion type silencer 20, made of an acrylic material, is a cavity body opened at one side. The opening 10 of the expansion chamber 201 fits the human face, shields the oronasal organs of the human, and is connected to the tube 202 on the airway. The opening is changed suddenly in cross section at the connection to form the discontinuous acoustic impedance, resulting in reflection and absorption of the noise of the snoring sound.

The active noise elimination module 30 further includes a secondary sound source 301, a microphone 302 and a control module 303, wherein the microphone 302 and the active noise elimination module 30 are of the feedback topological structures. The microphone 302 collects a deviation signal and sends it to the control module 303. The control module 303 can, but is not limited to, a filter. The deviation signal passes through the filter to output a drive signal opposite to the noise signal of the snoring sound to drive the secondary sound source 301 to send out an inverted sound wave which is overlapped with the noise of the snoring sound within the expansion chamber 201 to achieve the noise elimination function, which can achieve the embodiment of the present invention, i.e., a technical solution of the anti-snoring device based on an expansion type silencer.

It is to be understood that the tube 202 as the air inlet/outlet pipeline for breathing can be inserted into the expansion chamber 201 to improve the performance of the expansion type silencer 20. For example, the tube 202 is inserted into ¼ or ½ of the expansion chamber 201, and the tube 202 can be completely inserted into the expansion chamber 201, so that the tube 202 is attractive in appearance as it is not exposed.

It is to be understood that the control module 303 further includes an audio bypass module (also called a music compensation module; not shown in the figure). Noise of audio inputted by the audio bypass module is not actively eliminated in the expansion chamber, and the audio is subjected to electroacoustic energy exchange through the secondary sound source 301 to output the sound wave. The sound wave enters the nasal cavity. Because the nasal cavity is connected to the inner side of the eardrum of the human through the auditory tube and the middle ear cavity to cause vibration of the eardrum, the human has the auditory sense. Therefore, a person who uses the anti-snoring device provided by the present invention can listen to a berceuse or answer an incoming call or a ringing sound at the prone position, so that inconvenience caused by using the earphone to achieve the same function is overcome because the worn earphone is easy to fall off in the sleeping posture.

In addition, the active noise elimination module 30 further includes a button module (not shown in the figure), for example, a power switch for controlling the active noise elimination module 30, and at this time, a button sound effect is input into the audio bypass module 3031, so that the secondary sound source 301 sends out a special effect sound of the button, which improves the operating experience.

It is to be understood that in the closed cavity of the expansion chamber 201 jointly formed by the expansion chamber 201 opened at one side and the facial skin tissues shielded by the opening, because the skin has the mechanical elastic and the tissue friction force, the acoustic capacitance of the expansion chamber 201 and the acoustic resistance of passively absorbing noise are equivalently increased, which is equivalent to increase the size and the sound absorption material of the expansion chamber 201.

It is to be understood that when the human snores, the mouth will open and close periodically. The oral cavity and the cavity of the expansion chamber 201 are connected integrally as the mouth opens, so that the acoustic characteristic of the expansion chamber 201 changes periodically as well when the mouth opens and closes periodically, which adversely affects the noise reduction performance of the active noise elimination module 30. On the other hand, the sizes of the nasal cavity and the oral cavity vary with each individual, which adversely affects the noise reduction performance of the active noise elimination module 30 as well. Therefore, the embodiment is poor in applicability on crowds and human behaviors.

As shown in FIG. 9, to overcome the technical deficiencies of the first embodiment, the present invention provides a second embodiment of a anti-snoring device based on an expansion type silencer. Different from the first embodiment, the expansion chamber 201 further includes a division board 501 which divides the expansion chamber 201 into two cavities connected in series front and back, wherein the back cavity is an isolation chamber 50 interconnected to the front cavity expansion chamber 201 through the vent hole in the division board 501. The parameter Ma8 designed is relatively large to weaken or eliminate the influence of the acoustic mass Ma2 of the lip and the acoustic capacitance Ca2 of the oral cavity caused by periodical opening and closing of the mouth on the acoustic characteristic of the expansion chamber 201, which is beneficial to keeping the noise reduction performance of the active noise elimination module 30 stable, and avoiding the influence of individual differences between the oral cavities and the nasal cavities of different people on the noise reduction performance, thereby improving the applicability of the anti-snoring device provided by the present invention on crowds and human behaviors. Therefore, the present invention can be implemented, i.e., the technical solution of the anti-snoring device based on an expansion type silencer.

It is to be understood that the isolation chamber 50 and the expansion chamber 201 form the dual-cavity acoustic structure, i.e., the isolation chamber and the expansion chamber are connected in series, wherein the noise of the snoring sound is first subjected to the isolation chamber 50 to eliminate the high-mid frequency noise and then subjected to the expansion chamber and the active silencer to eliminate the low-mid frequency noise. Therefore, the size dimension of the expansion chamber can be made relatively small, and the size dimension of the isolation chamber can be made relatively large.

In conclusion, the anti-snoring device based on an expansion type silencer includes the expansion chamber, the pipe and the active noise elimination module, wherein the expansion chamber is connected to the active noise elimination module; the active noise elimination module further includes the secondary sound source, the microphone and the control module; one side of the expansion chamber is opened for hermetically shielding oronasal organs and forming the cavity of the expansion chamber with shielded facial skin. The pipe is the airflow passage for breathing, which is the acoustic device with acoustic impedance different from that of the expansion chamber. The present invention provides the anti-snoring device based on an expansion type silencer. First, the technical solution is proposed from the perspective of eliminating the "effect" in the causal relationship of snoring. In the technical field of snore stoppers, by adopting the noise elimination mode of expanded and active silencers, the technical deficiency that the noise elimination performance of the active silencer at the high-mid frequency band is reduced, the noise elimination performance of the expansion type silencer at the low-mid frequency band is reduced, and the bandwidth is insufficient is overcome, so that the anti-snoring device provided by the present invention gains beneficial effects of wide applicability, large noise elimination amount, wide noise elimination bandwidth, small size, light weight, and low electric energy consumption. Then, the active noise elimination module is detachably connected to the expansion chamber, which solves the problem of a peculiar smell caused by breathing when the expansion chamber is cleaned; further, the control module further includes the audio bypass module which propagates the sound wave converted by the audio to the inner side of the eardrum through the nasal cavity, the auditory tube and the middle ear cavity to cause vibration of the eardrum, so that the human has the auditory sense, which solves the problem that the earphone is easy to fall off when the human sleeps at a prone position. Finally, a serial dual-cavity acoustic construction is formed by additionally arranging the isolation chamber, which solves the problem of stability of noise elimination performance caused by mouth opening and closing behaviors and air leakage.

It should be noted that the present disclosure is not limited to the above embodiments. According to the creative spirit of the present disclosure, those skilled in the art can also make other modifications, which should not be interpreted as limiting the scope of the present disclosure. It should be noted that all modifications and substitutions equivalent to the embodiment should be included in the scope of the present disclosure. Therefore, the scope of protection of the present disclosure shall be subject to the scope defined in the claims.

What is claimed is:

1. An anti-snoring device based on an expansion type silencer, comprising:

an active noise elimination module, including a secondary sound source, a microphone and a control module;

an expansion chamber, connected to the active noise elimination module;

a tube, connected to the expansion chamber and functioning as an airflow passage for breathing;

an opening, used for hermetically shielding oronasal organs and forming an acoustic system of the expansion type silencer with hermetically shielded facial skin; and a division board, dividing the anti-snoring device into a front expansion chamber and a rear isolation chamber connected on an airway;

wherein the tube is an acoustic device with acoustic impedance different from that of the expansion chamber.

2. The anti-snoring device based on an expansion type silencer of claim 1, wherein the active noise elimination module and the expansion chamber are detachably connected.

3. The anti-snoring device based on an expansion type silencer of claim 1, wherein the division board comprise vent holes or vent pipes connected in the airway between the expansion chamber and the isolation chamber.

4. The anti-snoring device based on an expansion type silencer of claim 1, wherein noise of a snoring sound is first subjected to the isolation chamber to remove high-mid frequency components, and is then subjected to the expansion chamber to remove low-mid frequency components.

5. The anti-snoring device based on an expansion type silencer of claim 1, wherein the control module further includes an audio bypass module;

wherein audio input by the audio bypass module generates a sound wave in the expansion chamber through the secondary sound source, noise of the sound wave is not actively eliminated, the sound wave enters a nasal cavity, and is then propagated to the inner side of an eardrum through an auditory tube and a middle ear cavity to cause vibration of the eardrum, so that a human has an auditory sense.

6. The anti-snoring device based on an expansion type silencer of claim 5, further comprising a Bluetooth module respectively connected to the audio bypass module and external wireless equipment;

wherein the Bluetooth module inputs an audio signal from the external wireless equipment and then outputs the audio signal to the audio bypass module; and wherein the external wireless equipment includes a mobile phone, a computer and a tablet personal computer.

7. The anti-snoring device based on an expansion type silencer of claim 6, further comprising a voice pickup microphone connected to the Bluetooth module to pick up a human sound audio signal, and then the Bluetooth module outputting the human sound audio signal to the external wireless equipment.

8. The anti-snoring device based on an expansion type silencer of claim 1, wherein the active noise elimination module can close noise elimination of the high-frequency components of the noise of the snoring sound.

9. The anti-snoring device based on an expansion type silencer of claim 1, wherein topological structures of the microphone and the control module include feedforward, feedback and hybrid structures.

10. The anti-snoring device based on an expansion type silencer of claim 1, wherein the microphone is connected to one of or a combination of the front expansion chamber, the rear isolation chamber and the tube.

* * * * *